(12) United States Patent
Zhan et al.

(10) Patent No.: US 11,944,484 B2
(45) Date of Patent: Apr. 2, 2024

(54) MATERIAL DECOMPOSITION CALIBRATION METHOD AND APPARATUS FOR A FULL SIZE PHOTON COUNTING CT SYSTEM

(71) Applicant: CANON MEDICAL SYSTEMS CORPORATION, Otawara (JP)

(72) Inventors: Xiaohui Zhan, Vernon Hills, IL (US); Xiaofeng Niu, Vernon Hills, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 160 days.

(21) Appl. No.: 17/218,924

(22) Filed: Mar. 31, 2021

(65) Prior Publication Data
US 2022/0313203 A1 Oct. 6, 2022

(51) Int. Cl.
*A61B 6/00* (2006.01)
*A61B 6/03* (2006.01)
*A61B 6/42* (2024.01)
*A61B 6/58* (2024.01)

(52) U.S. Cl.
CPC .............. *A61B 6/583* (2013.01); *A61B 6/032* (2013.01); *A61B 6/4241* (2013.01)

(58) Field of Classification Search
CPC ........ A61B 6/583; A61B 6/032; A61B 6/4241
See application file for complete search history.

(56) References Cited

U.S. PATENT DOCUMENTS

| | | | |
|---|---|---|---|
| 2005/0084069 A1* | 4/2005 | Du | A61B 6/583 |
| | | | 378/98.9 |
| 2015/0182176 A1 | 7/2015 | Jin et al. | |
| 2018/0025515 A1 | 1/2018 | Shechter | |
| 2019/0313993 A1* | 10/2019 | Zhou | A61B 6/032 |
| 2020/0193654 A1 | 6/2020 | Yanoff et al. | |
| 2020/0261050 A1* | 8/2020 | Bornefalk | A61B 6/584 |
| 2020/0281543 A1* | 9/2020 | Sahbaee Bagherzadeh | |
| | | | G06T 11/005 |
| 2022/0211338 A1* | 7/2022 | Kojima | A61B 6/5217 |

FOREIGN PATENT DOCUMENTS

EP 3965059 A1 * 3/2022
WO WO 2018/002226 A1 1/2018

OTHER PUBLICATIONS

Emil Y. Sidky, et al., "A robust method of x-ray source spectrum estimation from transmission measurements: Demonstrated on computer simulated, scatter-free transmission data", Journal of Applied Physics, vol. 97, Issue 12, 2005, 7 pages (Abstract only).

Xinhui Duan, et al., "CT scanner x-ray spectrum estimation from transmission measurements", Medical Physics, vol. 38, No. 2, Feb. 2011, pp. 993-997.

Jannis Dickmann, et al., "A count rate-dependent method for spectral distortion correction in photon counting CT", SPIE Proceedings, Medical Imaging: Physics of Medical Imaging, vol. 10573, Mar. 9, 2018, 2 pages (Abstract only).

* cited by examiner

*Primary Examiner* — Christine S. Kim
(74) *Attorney, Agent, or Firm* — Oblon, McClelland, Maier & Neustadt, L.L.P.

(57) ABSTRACT

A method and a system for providing calibration for a photon counting CT detector forward model for material decomposition. Various slabs of predetermined material and path lengths are placed in the photon counting CT detector and scanned using one or more stationary X-rays to obtain calibration data and parametrize the forward model.

16 Claims, 11 Drawing Sheets

MATERIAL DECOMPOSITION CALIBRATION METHOD AND APPARATUS FOR A FULL SIZE PHOTON COUNTING CT SYSTEM

FIELD OF THE INVENTION

The disclosure relates to material decomposition in a full size photon counting computed tomography system.

DESCRIPTION OF THE RELATED ART

Computed tomography (CT) systems and methods are typically used for medical imaging and diagnosis. CT systems generally create projection images through a subject's body at a series of projection angles. A radiation source, such as an X-ray tube, irradiates the body of a subject and projection images are generated at different angles. Images of the subject's body can be reconstructed from the projection images.

Conventionally, energy-integrating detectors (EIDs) and/or photon-counting detectors (PCDs) have been used to measure CT projection data. PCDs offer many advantages including their capacity for performing spectral CT, wherein the PCDs resolve the counts of incident X-rays into spectral components referred to as energy bins, such that collectively the energy bins span the energy spectrum of the X-ray beam. Unlike non-spectral CT, spectral CT generates information due to different materials exhibiting different X-ray attenuation as a function of the X-ray energy. These differences enable a decomposition of the spectrally resolved projection data into different material components, for example, the two material components of the material decomposition can be bone and water.

Even though PCDs have fast response times, at high X-ray flux rates indicative of clinical X-ray imaging, multiple X-ray detection events on a single detector may occur within the detector's time response, a phenomenon called pileup. Left uncorrected, pileup effect distorts the PCD energy response and can degrade reconstructed images from PCDs. When these effects are corrected, spectral CT has many advantages over conventional CT. Many clinical applications can benefit from spectral CT technology, including improved material differentiation since spectral CT extracts complete tissue characterization information from an imaged object.

One challenge for more effectively using semiconductor-based PCDs for spectral CT is performing the material decomposition of the projection data in a robust and efficient manner. For example, correction of pileup in the detection process can be imperfect, and these imperfections degrade the material components resulting from the material decomposition.

In a photon counting CT system, the semiconductor-based detector using direct conversion is designed to resolve the energy of the individual incoming photons and generate measurement of multiple energy bin counts for each integration period. However, due to the detection physics in such semiconductor materials (e.g. CdTe/CZT), the detector energy response is largely degraded/distorted by charge sharing, k-escape, and scattering effects in the energy deposition and charge induction process, as well as electronic noise in the associated front-end electronics. Due to finite signal induction time, at high count-rate conditions, pulse pile-up also distorts the energy response, as discussed above.

Due to sensor material non-uniformity and complexity of the integrated detection system, it is difficult to accurately model such detector response for a PCD just based on physics theories or Monte Carlo simulations with a certain modeling of the signal induction process, which modeling determines the accuracy of the forward model of each measurement. Also, due to uncertainties in the incident X-ray tube spectrum modeling, the modelling introduces additional errors in the forward model, and all these factors eventually degrade the material decomposition accuracy from the PCD measurements, therefore the generated spectral images.

Calibration methods have been proposed to solve similar problems in literature. The general idea is to use multiple transmission measurements of various known path lengths to modify the forward model such that it agrees with the calibration measurements. Some ideas are applied on estimation of the X-ray spectrum in conventional CT, see Sidky et al., Journal of Applied Physics 97(12), 124701 (2005) and Duan et al., Medical Physics 38(2), February, 2011, and later adopted on photon-counting detectors to estimate the combined system spectral response, see Dickmann et al., Proc. SPIE 10573, Medical Imaging 2018: Physics of Medical Imaging, 1057311 (Mar. 9, 2018). However, there can be many variations in the detail design and implementation of the calibration method, especially considering the application feasibility in a full 3rd generation CT geometry.

SUMMARY

Disclosed is a calibration method comprising: placing at least one slab in a field of view of an X-ray scanner system, wherein the at least one slab has at least one known linear attenuation coefficient and at least one known pathlength; scanning, on the X-ray scanner system, the at least one slab with at least one X-ray tube located at plural known locations at different angles relative to the at least one slab; generating material decomposition data based on the scannings at the different angles; generating air calibration data based on at least one air scan using the at least one X-ray tube at at least one rotation speed; and calibrating a forward model for the X-ray scanner system based on the material decomposition data and the air calibration data.

In one embodiment, the at least one X-ray tube is stationary. In alternate embodiments, the at least one X-ray tube includes plural X-ray tubes.

In one embodiment, the material decomposition data includes a weighted bin response and a pulse pileup correction term.

In one embodiment, the forward model includes a weighted bin response, a pulse pileup correction term, the at least one known linear attenuation coefficient, the at least one known pathlength, and the air calibration data.

In one embodiment, the at least one slab is placed level in the field of view of the X-ray scanner system.

In one embodiment, the at least one slab fully covers the field of view of the X-ray scanner system.

One embodiment further comprises scanning, after the calibrating of the forward model for the X-ray scanner system, an object.

In one embodiment, the X-ray scanner system is a photon counting CT scanner system, such as a $3^{rd}$ generation photon counting CT scanner system.

In one embodiment, the at least one slab is made up of multiple materials. In another embodiment, the at least one slab includes a plurality of slabs with different heights.

Also disclosed is a system comprising: at least one slab placed in a field of view of an X-ray scanner system, wherein the at least one slab has at least one known linear attenuation coefficient and at least one known pathlength; and processing circuitry configured to, scan, on the X-ray scanner system, the at least one slab with at least one X-ray tube located at plural known locations at different angles relative to the at least one slab; generate material decomposition data based on the scannings at the different angles; generate air calibration data based on at least one air scan using the at least one X-ray tube at at least one rotation speed; and calibrate a forward model for the X-ray scanner system based on the material decomposition data and the air calibration data.

In one embodiment, the at least one X-ray tube is stationary.

In one embodiment, the material decomposition data includes a weighted bin response and a pulse pileup correction term.

In one embodiment, the forward model includes a weighted bin response, a pulse pileup correction term, the at least one known linear attenuation coefficient, the at least one known pathlength, and the air calibration data.

In one embodiment, the at least one slab is placed level in the field of view of the X-ray scanner system.

In one embodiment, the at least one slab fully covers the field of view of the X-ray scanner system.

In one embodiment, the processing circuitry is further configured to scan, after the calibrating of the forward model for the X-ray scanner system, an object.

In one embodiment, the X-ray scanner system is a photon counting CT scanner system, such as a $3^{rd}$ generation photon counting CT scanner system.

In one embodiment, the at least one slab is made up of multiple materials. In another embodiment, the at least one slab includes a plurality of slabs with different heights.

BRIEF DESCRIPTION OF THE DRAWINGS

The application will be better understood in light of the description which is given in a non-limiting manner, accompanied by the attached drawings in which.

DETAILED DESCRIPTION OF THE PREFERRED EMBODIMENTS

Reference throughout this specification to "one embodiment" or "an embodiment" means that a particular feature, structure, material, or characteristic described in connection with the embodiment is included in at least one embodiment of the application, but do not denote that they are present in every embodiment.

Thus, the appearances of the phrases "in one embodiment" or "in an embodiment" in various places throughout this specification are not necessarily referring to the same embodiment of the application. Furthermore, the particular features, structures, materials, or characteristics may be combined in any suitable manner in one or more embodiments.

This disclosure relates to a photon counting CT scanner system for material decomposition, said CT scanner system comprising one or more X-ray tubes that emit X-ray radiation, and an array of detector pixels for receiving the X-ray radiation propagating through a field of view of the CT scanning system.

Figure 1:
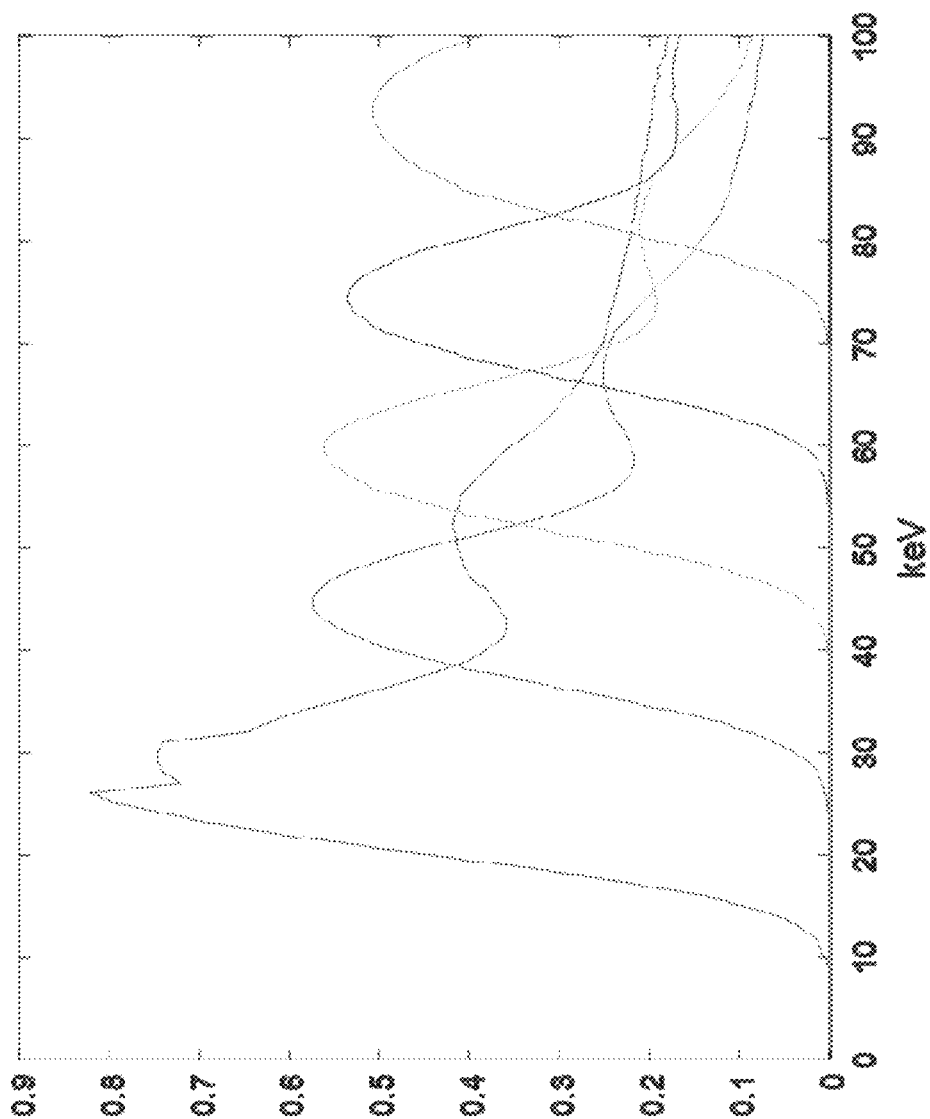
FIG. 1 shows an example of a PCD bin response function $S_b(E)$ for a photon counting detector. Each curve stands for an example function for each energy bin.

In a transmission measurement using a photon counting energy-resolving detector (PCD), the forward model can be formulated as below:

$$N_b(l_1, \ldots, _M) = N_0 \times \int dE(E) S_b(E) \exp(-\Sigma \mu_m l_m), \quad (1)$$

where $S_b(E)$ denotes the bin response function defined as $S_b(E) = \int_{E_{bL}}^{E_{bH}} R(E,E') dE'$ where $R(E,E)$ is the detector response function, and $E_{bL}$ and $E_{bH}$ are the low and high energy threshold of each counting bin. FIG. 1 shows an example model of a typical $S_b(E)$ function for a PCD, where a long tail above the energy window is induced by charge sharing, k-escape and scattering effect. The low energy tail is mostly due to the finite energy resolution from the associated electronic noise. $N_0$ is the total flux from an air scan, $\mu_m$ and $l_m$ are the $m^{th}$ basis material linear attenuation coefficient and path length. $w(E)$ is the normalized incident X-ray spectrum. In practice, both $w(E)$ and $S_b(E)$ are not exactly known, and they can be combined as one term, $S_{wb}(E) = w(E) S_b(E)$, called thereafter the weighted bin response function. If $S_{wb}(E)$ can be calibrated through measurements, the decomposition problem at low flux condition can be well solved.

For a high flux scan condition (e.g. a few percent of pulse pileup), pulse pileup introduces additional spectral distortion in the measurement. One way to correct for the pileup effect is to introduce additional correction terms (e.g. see Dickmann above, who uses the measured count rate(s) as input). And this type of additional calibration is based on an accurate estimation of the flux independent weighted bin response $S_{wb}(E)$. How to estimate $S_{wb}(E)$ in a full size 3rd generation CT system is a first problem solved in the present application.

At typical CT clinical scan conditions, it is common to encounter a few percent or higher pulse pileup for some measurements. The resulting effect in material decomposition depends on the measured spectrum as well as the flux. Without knowing the actual detector response, one can only do a limited number of transmission measurements to adjust the forward model. For a full CT system in clinical setting, it is crucial to have a feasible calibration procedure. Therefore, how to efficiently parameterize the model and optimize the calibration procedure is the second problem solved in the present application.

Additional practical challenges of conducting such a two-step calibration in a full size CT system include the following: fan-angle dependent weighted spectral response due to beam pre-filtration (e.g. bowtie filters); minimum flux limited due to the X-ray tube operational specifications and fixed system geometry; full detector ring calibration with various detector response across the pixels; limited space for in-system calibration phantom positioning; complication when calibrating on a rotating system with anti-scatter-grids; calibration systematic error and related mechanical design tolerances; non-ideal detectors with uniformity issue on energy resolution, counting, and drifts of the energy threshold settings, etc.

The above non-ideal factors need to be considered for a photon counting CT to reach image qualities competitive to conventional energy integrating detector (EID)-based systems which have much simpler detector response modeling and related calibrations, while maintaining a similar calibration procedure/workflow that does not significantly increase the system down time.

In one non-limiting embodiment, a two-step calibration method for the PCD forward model for material decomposition is applied. The method consists of two parts: 1) estimation of the flux independent weighted bin response function $S_{wb}(E)$ using the expectation maximization (EM) method, and 2) estimation of the pileup correction term $P_b(E, N_b, N_{tot})$ which is a function of energy (E) and the measured bin counts ($N_b$, $N_{tot}$), where $N_b$ is the individual bin count and $N_{tot}$ is the total count of all the energy bins. The calibrated forward model can be expressed as:

$$N_b(l_1, \ldots, l_M) = N_0 \int^{E_{max}} dE S_{wb}(E) * P_b(E, N_b, N_{tot}) \exp(-\Sigma \mu_m l_m) \quad (2)$$

Here, instead of using only two materials, the method uses 2-5 different materials such as polypropylene, water, aluminium, titanium/copper, and k-edge materials to calibrate the weighted bin response function $S_{wb}(E)$ at low flux. With more selective materials used in the calibration, the number of total path lengths is reduced to achieve equivalent or better results.

Step 1: With an appropriate tube spectrum modelling to capture the characteristic peaks in the incident spectrum, and a physical model to simulate the photon-counting detector spectral response, an initial guess of $S_{wb}(E)$ can be produced. By using the EM method (e.g., see Sidky), $S_{wb}(E)$ can be reliably estimated for this very ill-conditioned problem based on a few transmission measurements.

Here, $P_b(E, N_b, N_{tot})$ is assumed to be constant in Step 1. The calibrated forward model can be simplified to a system of linear equations $$N_b(l_1, \ldots, l_M) = N_0 \int^{E_{max}} dE S_{wb}(E) \exp(-\Sigma \mu_m l_m) \quad (3)$$

Usually, the number of data measurements (M) is much smaller than the number of unknowns ($E_{max}$). With the assumption of Poisson distribution of the data acquisition, an iterative EM algorithm can be derived to find the optimal estimation of the unknown energy bin response function $S_{wb}(E)$, as described below.

When estimating the bin response function using low flux data acquisition, the pileup effect correction $P_b$ is assumed to be a known term (e.g. constant). So, the model is simplified to $$N_b = N_0 \int dE S_{wb}(E)[\exp[-\Sigma \mu_m(E) l_m]] \quad (4)$$

Let $A^j(E) = \exp[-\Sigma \mu_m(E) l_m^j]$ represent the attenuated pathlength for j-th measurement. Thus, for each measurement j, we have $$N_b^j = N_0 \int dE S_{wb}(E) A^j(E) = N_0 \Sigma_E S_{wb}(E) A^j(E) \quad (5)$$

With M measurements, the data acquisition can be written in the matrix form below $$N_0 \begin{pmatrix} A^1(1) & \cdots & A^1(E_{max}) \\ \vdots & \ddots & \vdots \\ A^M(1) & \cdots & A^M(E_{max}) \end{pmatrix}_{M \times E_{max}} \cdot \begin{pmatrix} S_{wb}(1) \\ \vdots \\ S_{wb}(E_{max}) \end{pmatrix}_{E_{max} \times 1} = \begin{pmatrix} N_b^1 \\ \vdots \\ N_b^M \end{pmatrix}_{M \times 1}$$

or $A \cdot S_{wb} = N_b$

By applying the EM iterative algorithm, the $S_{wb}$ can be estimated by $$S_{wb}^{(k+1)} = S_{wb}^{(k)} \odot ((A^T \cdot (N_b \oslash (A \cdot S_{wb}^{(k)}))) \oslash (A^T \cdot 1)) \quad (6)$$

where
k: iteration number
·: matrix multiplication
⊙: element-wise multiplication
⊘: element-wise division
1: vector of ones with size of M×1
the updating formula for $S_{wb}(E)$ is given by $$S_{wb}^{(k+1)}(E) = S_{wb}^{(k)}(E) \frac{\sum_{j'} A^{j'}(E) \frac{N_b^{j'}}{\sum_{E'} A^{j'}(E') S_{wb}^{(k)}(E')}}{\sum_{j'} A^{j'}(E)} \quad (7)$$

Step 2: Once $S_{wb}(E)$ is estimated from the calibration at each tube voltage (kVp) setting for each detector pixel, it is saved as a software calibration table on the system. It will be used as an input to further estimate the pileup correction terms $P_b(E, N_b, N_{tot})$ at higher flux scans. Both tables are then used for the material decomposition in object/patient scans to estimate the basis material path lengths.

The calibration tables are updated from time to time based on the system/detector performance variations. This can also be designed as an iterative procedure. If the image quality is not good enough on a quality check phantom, this calibration process is repeated with the updated calibration tables from the last iteration as the initial guess.

Figure 2:
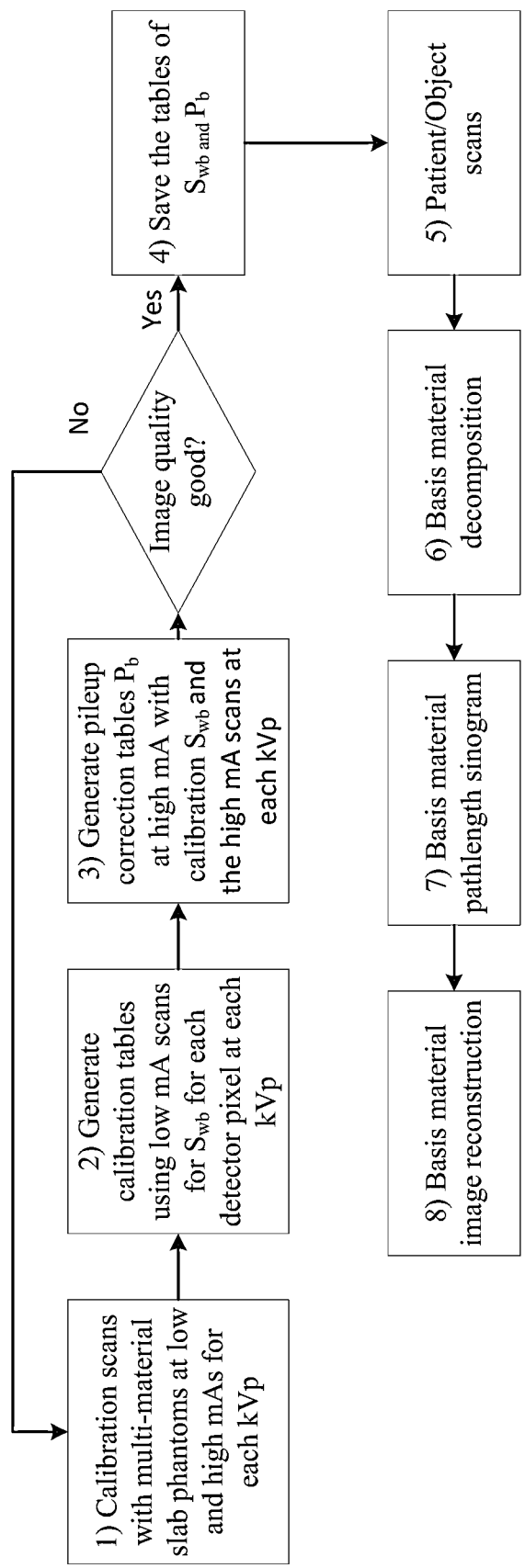
FIG. 2 shows a material decomposition calibration and processing workflow.

The high level workflow of the above process is demonstrated in FIG. 2. Steps 1) to 4) represent the calibration workflow, and steps 5) to 8) demonstrate how the calibration tables are used in the operational scans of patients/objects to produce spectral images.

First, a series of low flux scans on various material slabs are collected at each tube kVp setting, which is the peak potential applied on the X-ray tube. Typical CT systems support a few kVp settings from 70 to 140 kVp which generate different energy spectrums from the X-ray tube for different scan protocol. For a CT scan, both mA and kVp need to be pre-selected before the tube is turned on. Then, the low flux weighted bin response function $S_{wb}$ is estimated and with the estimated $S_{wb}$, the high flux slab scans are used to estimate the additional parameters in the pileup correction term $P_b$. With the estimation calibration tables of $S_{wb}$ and $P_b$ for each detector pixel, the quality of the calibration is checked on a quality phantom, e.g. a uniform water phantom, or phantom with multiple inserts with uniform known materials. The image quality is assessed with predefined standards, and if it is passed, the current calibration tables are saved and then used for the following patient/object scans data processing. Otherwise, the procedure goes through the first three steps again using the last iteration of $S_{wb}$ and $P_b$ as the initial guess. Here, commonly examined standards are: image CT number accuracy, uniformity, spatial resolution, noise and artifacts. To check the quality of this calibration, these metrics should all be checked, especially the accuracy and artifacts like ring or bands in the image, which indicate the calibration is not good enough.

Figure 3:
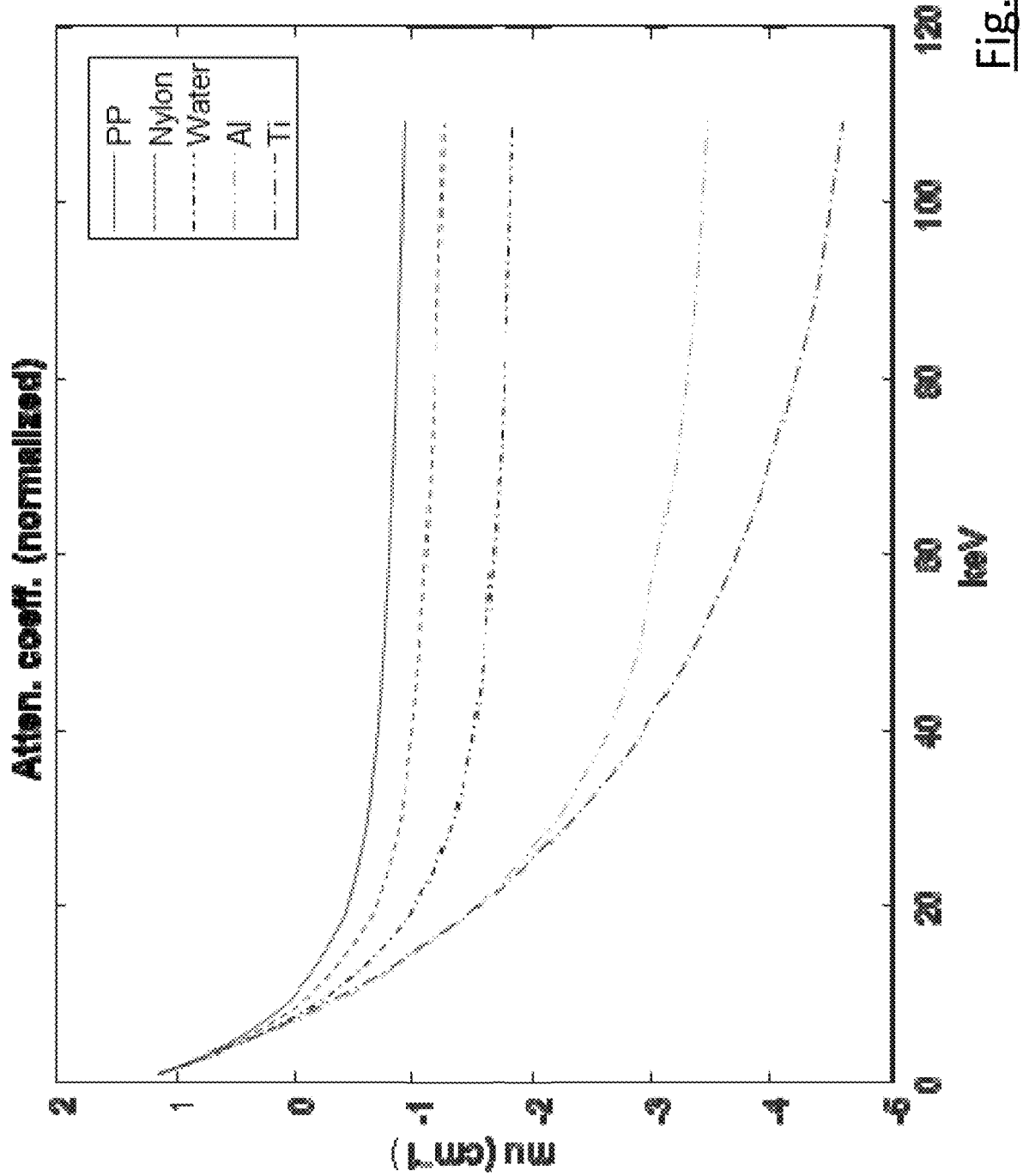
FIG. 3 shows normalized linear attenuation coefficients for different materials.

To choose the optimal materials and path lengths for this calibration, one can use the normalized linear attenuation coefficient vs. energy curves (FIG. 3) to choose the ones that are different from each other, e.g. polypropylene, water, aluminum, titanium can be a good group of combinations for such calibrations which covers a large range of common materials present in human body.

In order to satisfy the low flux condition through the calibration measurement to minimize the pileup effect in the flow diagram, step 1, one can select to use $n\tau < x$, where $x \sim 0.005-0.01$ and n is the pixel count rate with the lowest tube flux setting, and $\tau$ is the effective dead time of the PCD Application Specific Integrated Circuit (ASIC). By satisfying this condition, one can calculate the shortest path length of each selected calibration material, and the rest of path lengths can either be selected by equal spacing in path length or in resulting measurement count rate.

Figure 4:
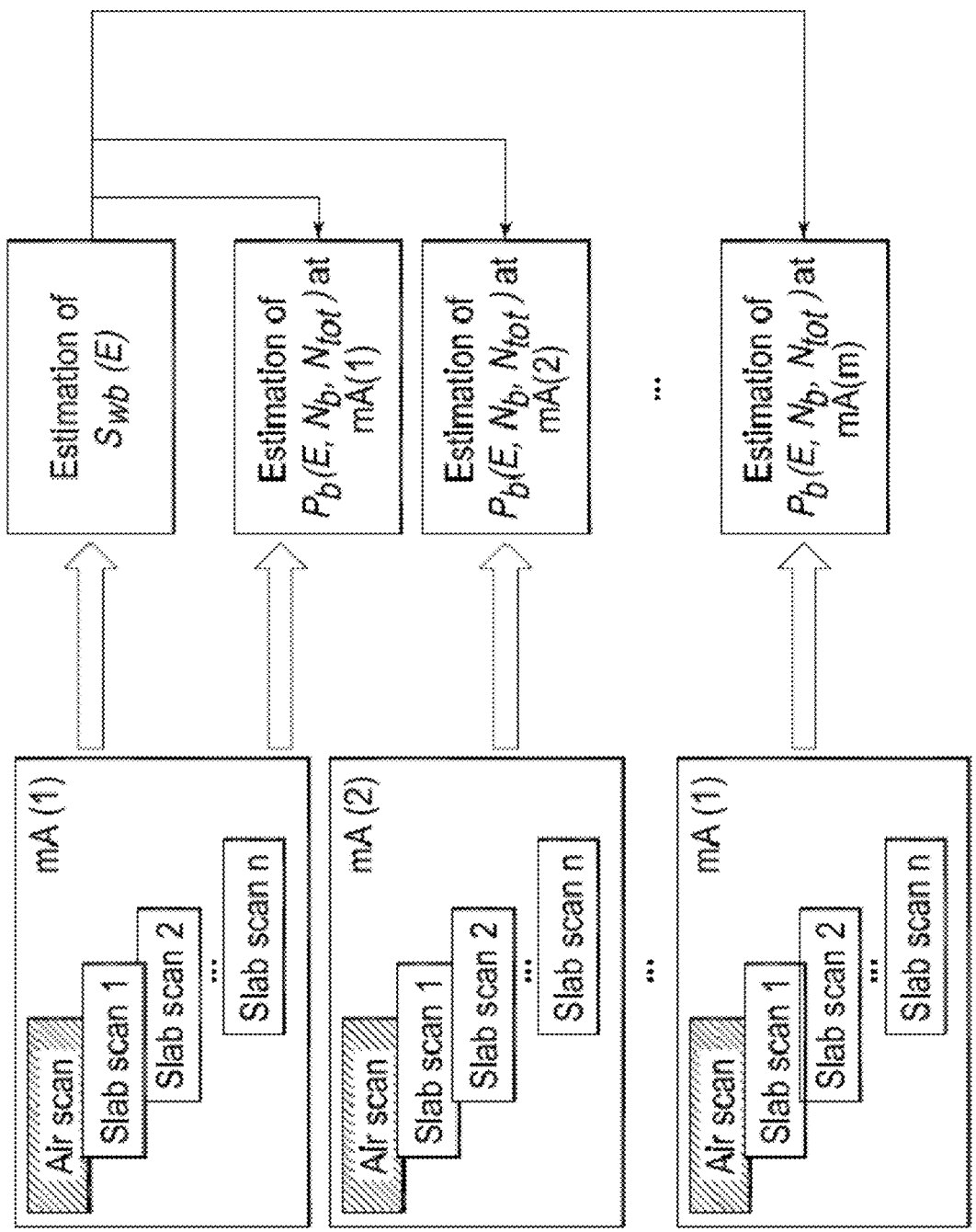
FIG. 4 shows a schematic of a calibration structure design, where the pileup correction tables $P_b$ are generated and used for each current (mA) individually.
Figure 5:
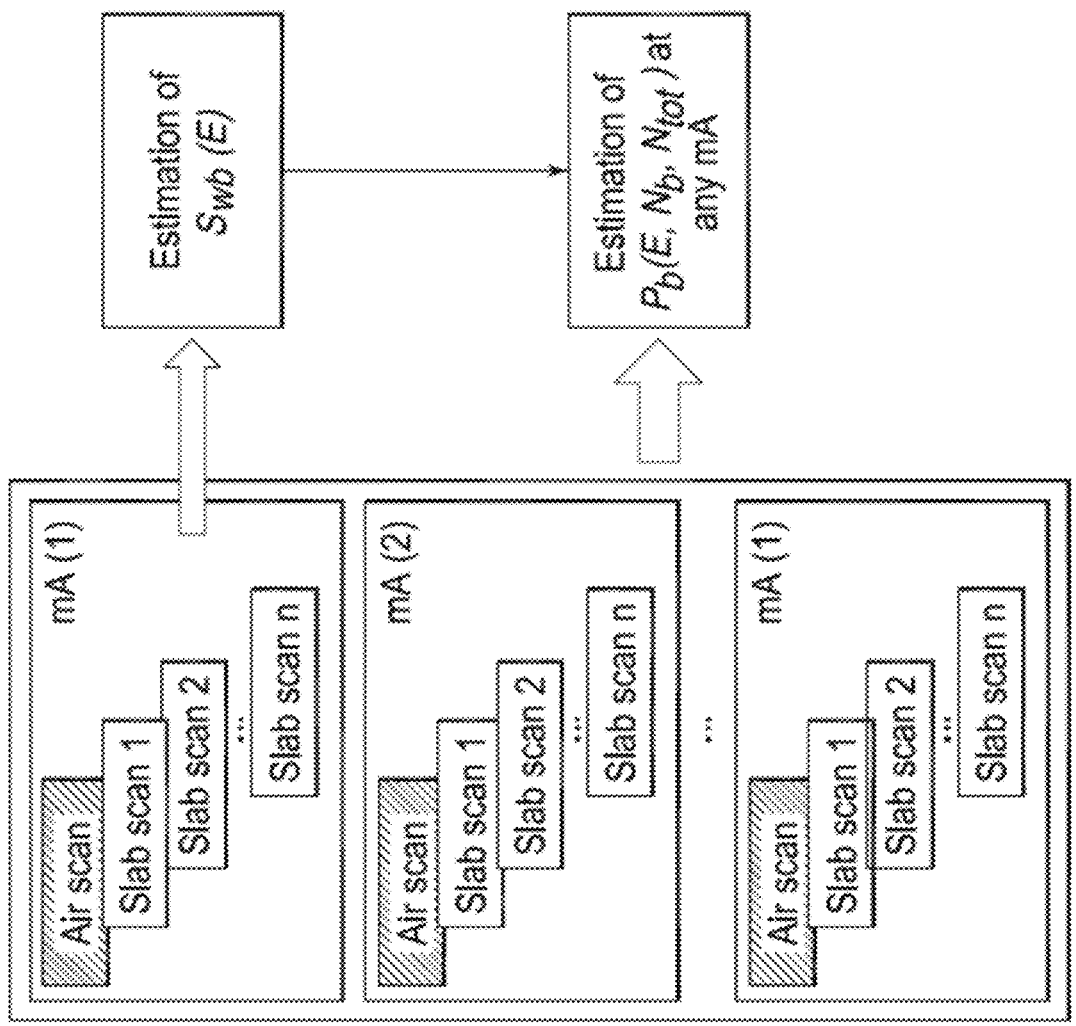
FIG. 5 shows a schematic of another calibration structure design, where a universal pileup correction table $P_b$ is generated for the entire current (mA) range.

For calibration of the pileup correction term $P_b$ in step 3, the same slab material and path lengths are used for scans at high mA settings. The calibration data can be grouped for each mA and generate different correction tables for each mA setting (FIG. 4), or include measurements at all flux ranges (e.g., from low to high mA, from high to low mA, or with most frequently used values first) to generate a universal correction table for a continuous mA setting (FIG. 5).

The calibration measurements should be taken with sufficient statistics to minimize the influence of the statistical fluctuation. One non-limiting example is to use >1000 times more statistics as the typical integration period for the calibration data sets to minimize the transferred statistical error in the calibration. Each energy bin b of the calibration measurements will be used to update the corresponding $S_{wb}(E)$ and $P_b(E, N_b, N_{tot})$.

Since one can only do limited number of measurements with a few energy bins, the estimation is very ill-conditioned. In this case, a good initial guess is crucial for an accurate estimation as it provides additional constraints for the EM method. One of the design variations to accommodate non-ideal detectors is to allow a more flexible energy window for each bin in the initial guess of $S_b$, especially with small variations in the actual energy threshold setting of the ASIC. By setting the low threshold x keV lower, and high threshold y keV higher, the initial $S_b$ becomes:

$$S_b(E) = \int_{EbL-x}^{EbH+y} R(E,E') dE' \qquad (8)$$

where x, y can be chosen between 5 to 10 keV to allow certain variations in the ASIC performance, while still providing additional constraints for the EM problem.

The design described in the present application employs more than two materials in the calibration, which provides more sensitivity to constraint the weighted bin response function estimation problem of the photon counting detectors.

In addition, the method utilizes a different parameterization for the high flux pileup correction terms $P_b$ which is now a function of E, $N_b$ and $N_{tot}$. The total count term $N_{tot}$ is introduced for a better approximation of the true pileup phenomena, and can significantly improve the model capability at higher flux condition with fewer parameters.

In addition, it is further possible to calculate an initial guess of the weighted bin response function by enlarging the energy threshold window, to accommodate non-ideal detector/ASIC performance.

A two-step calibration method for a PCD forward model for material decomposition is proposed. It consists of two parts: 1) estimation of the flux independent weighted bin response function $S_{wb}(E)$ using the state of the art EM (expectation maximization) method; and 2) estimation of the pileup correction term $P_b(E, N_b, N_{tot})$, which is a function of energy (E) and the measured bin counts ($N_b$, $N_{tot}$), where $N_b$ is the individual bin count and $N_{tot}$ is the total count of all the energy bins. The calibrated forward model can be expressed as shown in Equation (2).

Furthermore, to calibrate the forward PCD measurement model in Equation (2), in one embodiment, at least one slab of at least one predetermined material and known thickness is placed level in the CT scanner's field of view. By using a slab of predetermined material, the linear attenuation coefficient of the slab may be known. Further, by knowing the thickness of the slab, X-ray radiation path lengths through the slab may be known. The slab measurements can be performed by stationary scans where the X-ray tube is parked at a fixed location on the CT scanner and operating at various flux levels.

In one embodiment, the slab scans can also be taken at multiple fixed X-ray tube locations to increase the path length samples and coverage using the same slabs.

To apply for the patient/object scans when gantry is rotating, additional air scans can be taken at each rotation speed to correct for the additional shadow effect for each pixel when the anti-scatter-grid (ASG) is deflected under rotation. The air scans could produce air calibration tables, which may include data on the number of photons that arrive, per integration period, for each pixel.

For a full ring calibration in a 3rd generation geometry, due to the bowtie filtering and typical scanning object shape, the path length of the calibration materials for peripheral detectors may be designed differently from central detectors. Thinner path length ranges could be used towards the edge of the fan beam, and a relationship of the path lengths range for each material can be derived based on the material and shape of the bowtie filter. Additionally, a multi-material slab phantom may be designed to implement the calibration measurements.

Figure 6:
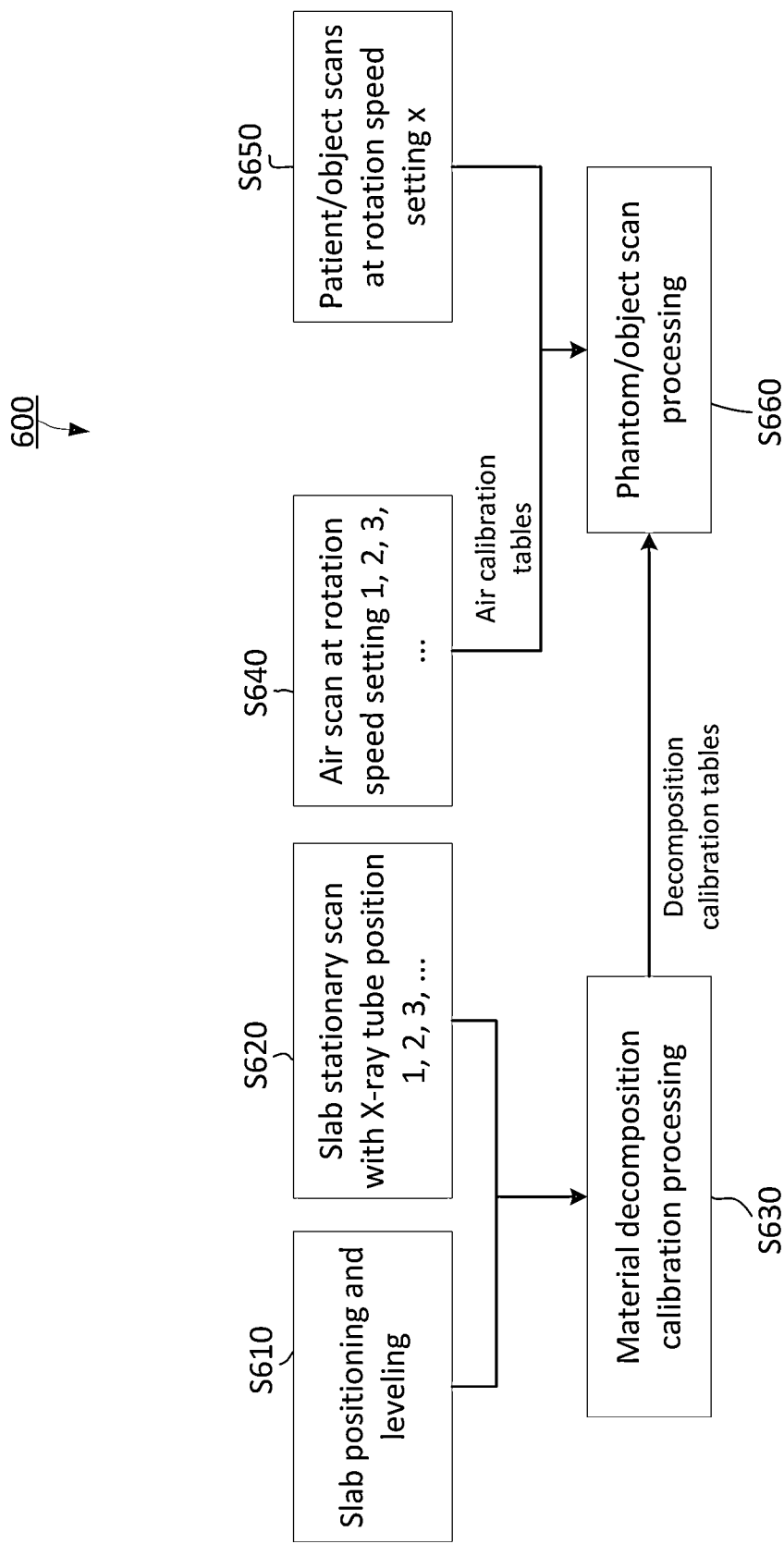
FIG. 6 shows a calibration scan procedure.

FIG. 6 shows one embodiment of a calibration method 600. In step S610, a slab of known material is first positioned and levelled on a CT scanner's patient couch such that path lengths are known and controlled. Then, in S620, one or more stationary X-ray tubes positioned on the CT gantry (e.g. three different X-ray tubes at three different positions) scan the slab. From the scans, in next step S630, material decomposition calibration processing is performed to produce decomposition calibration tables, as mentioned above. Furthermore, in S640, air scans are performed at a range of rotation speeds to produce air calibration tables. In S650, patient/object scans (at a known rotation speed) can be gathered. The decomposition calibration tables, air calibration tables, and patient/object scans can then be used in S660 for phantom/object scan processing and utilize a calibrated forward model.

The range of the slab calibration path length (L) may be designed to cover the maximum attenuation length in clinical scans (e.g. $L_{water}=0.1-40$ cm, $L_{bone}=0.1-10$ cm). This can be estimated through a group of representative clinical scans for different scan protocols. This range can be fan angle dependent, as the edge of the field of view (FOV) usually goes through much less attenuation compared to the center due to the typical patient shape and size. The selection of the calibration path length range can depend on different imaging task which focus on different anatomy. The calibration path length range can also be universal across the fan angle to better cover the abnormal case where the patient is either oversized or needs to be largely shifted from the iso-centre. In other words, various calibration path length ranges may be used at different fan angles to improve the calibration accuracy and efficiency. The slab scans used for the forward model calibration can be selected based on the imaging task to generate the best image quality.

Figure 7:
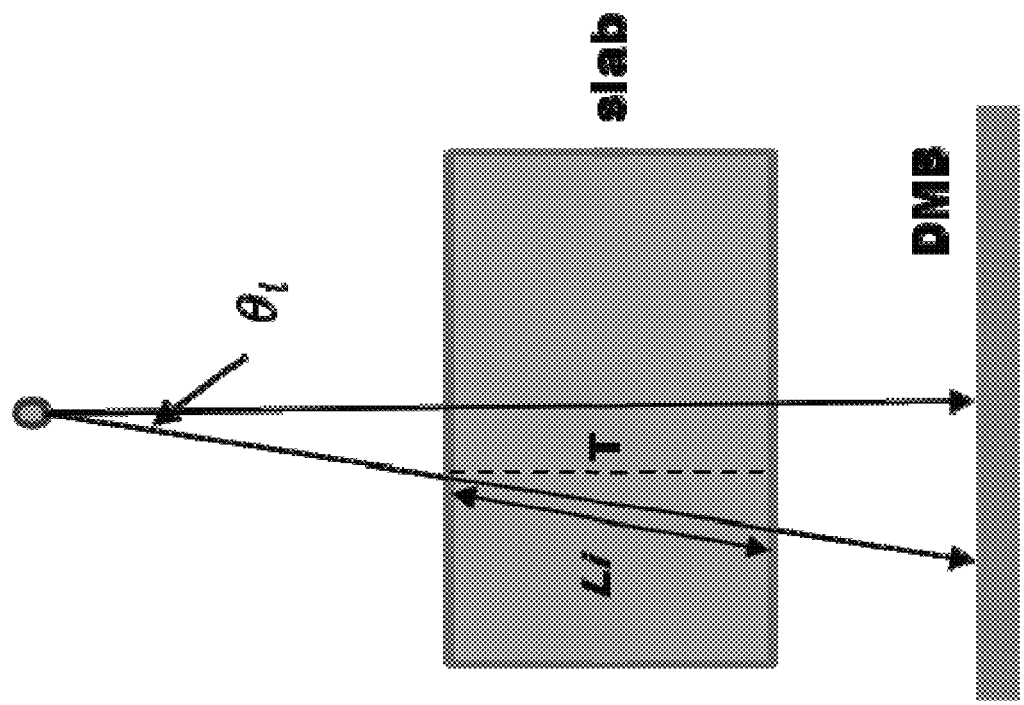
FIG. 7 illustrates calibration slab path lengths at different detector pixels.

With a typical fan beam coverage in a 3rd generation CT, flat slabs are used for this calibration with slightly different actual path lengths across the detector array, as shown in FIG. 7. The actual path lengths $L_i$ for each detector pixel of these calibration scans can be calculated by:

$$L_i = T/\cos \theta_i \qquad (9)$$

where T is the thickness of the calibration slab, and $\theta_i$ is the projected fan angle of detector pixel i on a detector module blade (DMB), wherein the DMB consists of rows and channels.

In order to minimize the path length error, calibration with different slabs and thicknesses may be done using a static scan configuration without rotation. The slabs should be large enough to cover the entire detector array and kept well levelled during the entire data acquisition. If for thick slabs, the CT gantry bore size does not allow for a single slab position to cover the entire detector surface, the slab position can be adjusted and multiple scans can be used to cover the entire detector surface. In another embodiment, the calibration with different slabs and thickness may be done using a scan configuration with rotation.

The additional system variations (e.g. tube flux, ASG shadow, etc.) with different rotation speed may be captured by air scans and a reference detector, and corrected accordingly in the air flux term $N_0$ of the forward model. For example, air scans at each rotation speed may be performed prior to the patient/object scan to calibrate the ASG deflection, as well as other beam path variations during rotation that induce the incident flux variation across the detector at different views.

Figure 8:
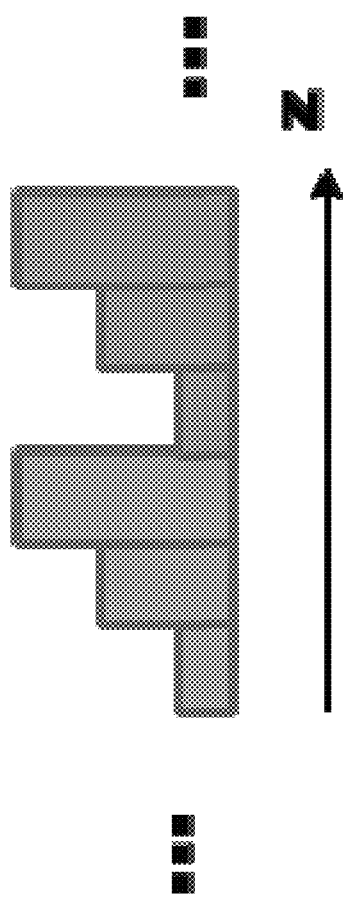
FIG. 8 shows an example of a calibration slab design where calibration slabs are lined up in a Z-direction along at least a portion of a patient couch or other movable mechanism within the detector field.

Referring to FIG. 8, the various calibration slabs can be combined together in a direction along at least a portion of the length of the patient couch to become a long "wedge-like" phantom, so that by moving the position of the couch (or whatever transport mechanism is conveying the slabs), each calibration path length can be detected without re-aligning the phantom, thereby accelerating the calibration process.

Figure 9:
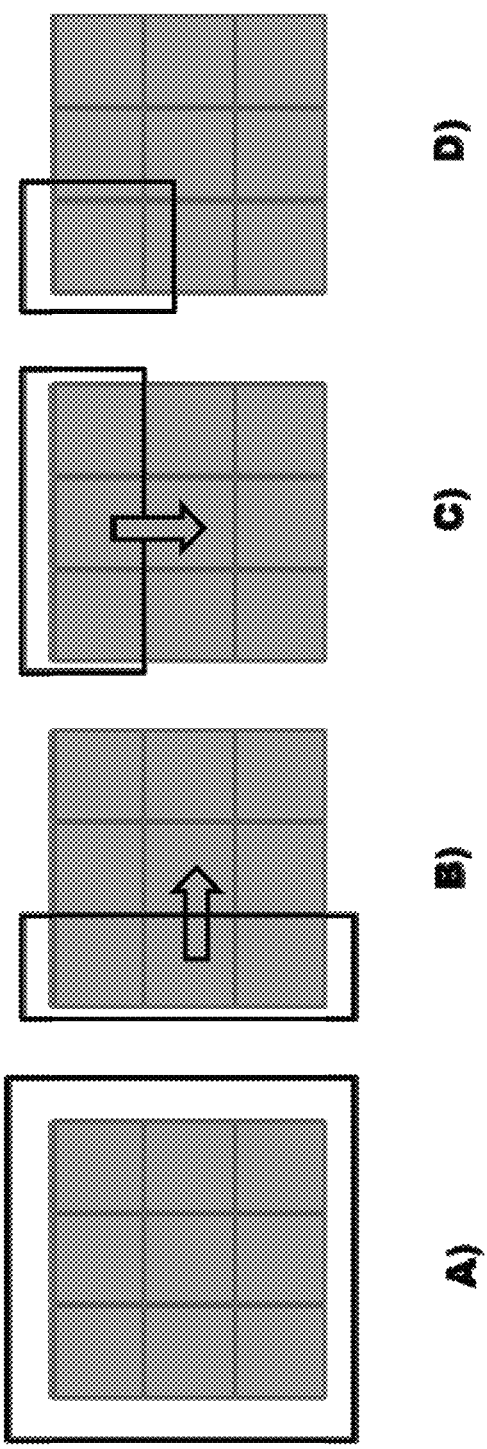
FIG. 9 shows various summing schemes that may be used for decomposition calibration and processing.

To capture the spectrum variation across the fan beam after bowtie filter and detector response variation across different detector pixels, this calibration process may be done pixel by pixel with each bowtie/filter configuration. For a combined-pixel mode ($N_T \times N_C$), this calibration can be done based on the measurement of the sum (or average) of combined pixels for each filter configuration. For example, FIG. 9 shows various summing schemes for decomposition calibration and processing, where the following object scan material decomposition can choose to use one of the summing patterns with the corresponding calibrated tables. The illustrated summing schemes in FIG. 9 are A) summing over the macro-pixel pitch, e.g. 3×3 combined mode, B) summing over the row direction, e.g. 1×3 combined mode, C) summing over the channel direction, e.g. 3×1 combined mode, and D) calibration based on individual micro pixel, e.g. 1×1.

Figure 10:
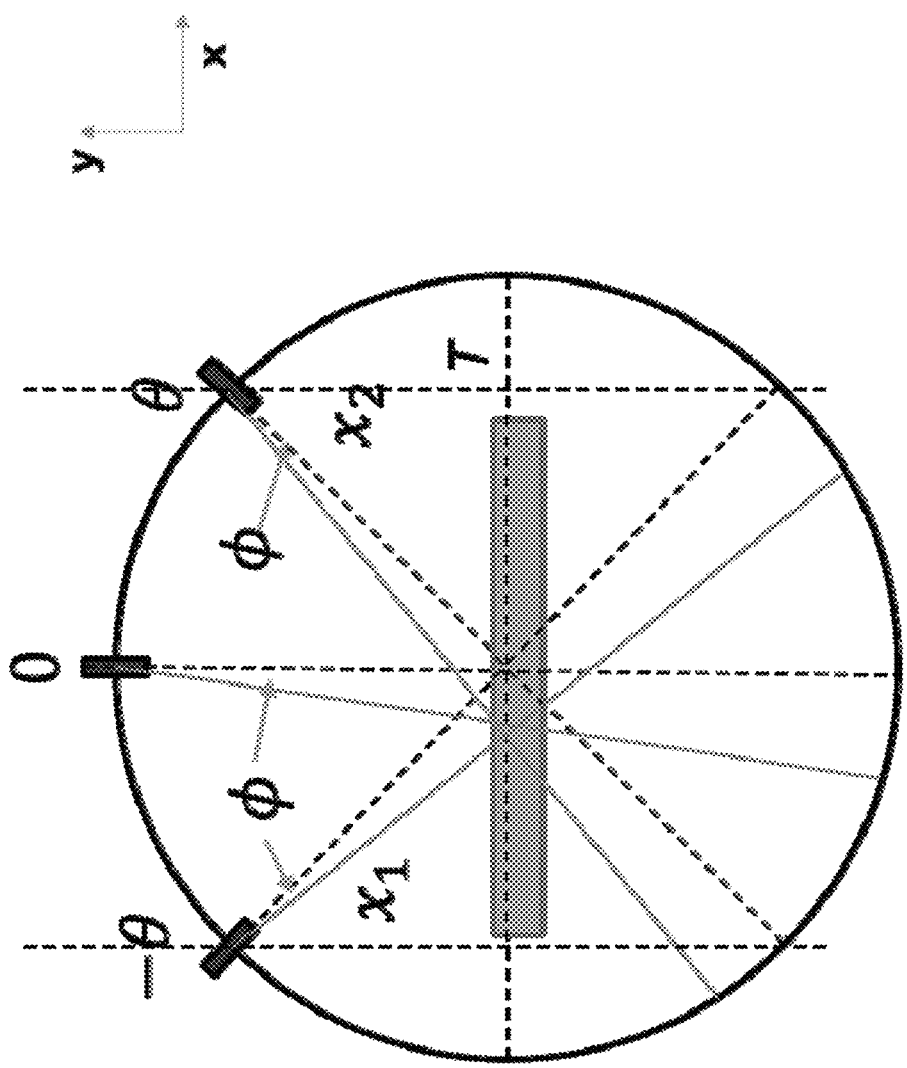
FIG. 10 is a schematic that shows how different X-ray tube locations can generate different path lengths for a slab scan during calibration.

To increase the calibration path length combinations for each slab configuration, the X-ray tube can be positioned at various locations while the slabs are fixed and levelled in the X-Y plane, as illustrated in FIG. 10, which is a schematic showing how multiple tube locations can generate different path lengths for the slab scan in this calibration. As an example, for a given slab thickness T, at detector pixel i, which is located at fan angle $\theta_i$, when the tube is placed at different positions ($-\theta$, 0, $\theta$), the measured path lengths are given by:

$$L_i(-\theta) = \frac{T}{\cos(x_1)};$$

$$L_i(0) = \frac{T}{\cos(\phi)};$$

$$L_i(\theta) = \frac{T}{\cos(x_2)};$$

where $x_1 = \theta - \phi$, $x_2 = \theta + \phi$. In one embodiment, the typical range of $\phi$ could be between 0 to 25 degree, and $\theta$ can be selected between 20 to 60 degrees depending on the slab thickness intervals. By using this park and shoot scheme, it can triple the path length samples for most of the detector channels, hence, greatly reduced the number of calibration slabs needed to cover the same or larger path length range. The tube can also park at more than three positions to further increase the calibration samples, following the same calculation method described above. For a wide cone coverage system, the calibration path length needs to be calculated based on the projected angle at both the channel and the row direction.

In one embodiment, the slabs are flat and kept levelled during the calibration; this is because it reduces/controls the uncertainty of the path length. In another embodiment, the slabs do not necessarily have to be flat nor level, so long as the path lengths are known and controlled. Further, in one embodiment, each of the slabs are made up of a single material. In another embodiment, the slabs do not always have to consist of a single material. For example, a slab could comprise multiple materials. Examples of materials for a slab can include polypropylene, water, aluminium, titanium/copper, tissue surrogates, other polymers, stainless steel or other metals, k-edge materials, and various tissue mimicking materials.

The at least one slab can also be laid out in a variety of ways to obtain multiple pathlengths from one or more materials. For instance, multiple slabs can be lined up adjacently along the patient couch for scanning as the patient couch moves within a radiography gantry. The multiple slabs can be of the same height with multiple materials, multiple heights with the same material, or multiple heights with multiple materials. In another exemplary embodiment, slabs can be held and suspended in the CT apparatus field of vision (e.g. using a robotic arm). In another exemplary embodiment, multiple slabs can be lined up with a shift in z-direction between each two adjacent slabs. As the slabs move in and out of the scanning field of vision, multiple stepwise pathlength data can be acquired continuously.

Figure 11:
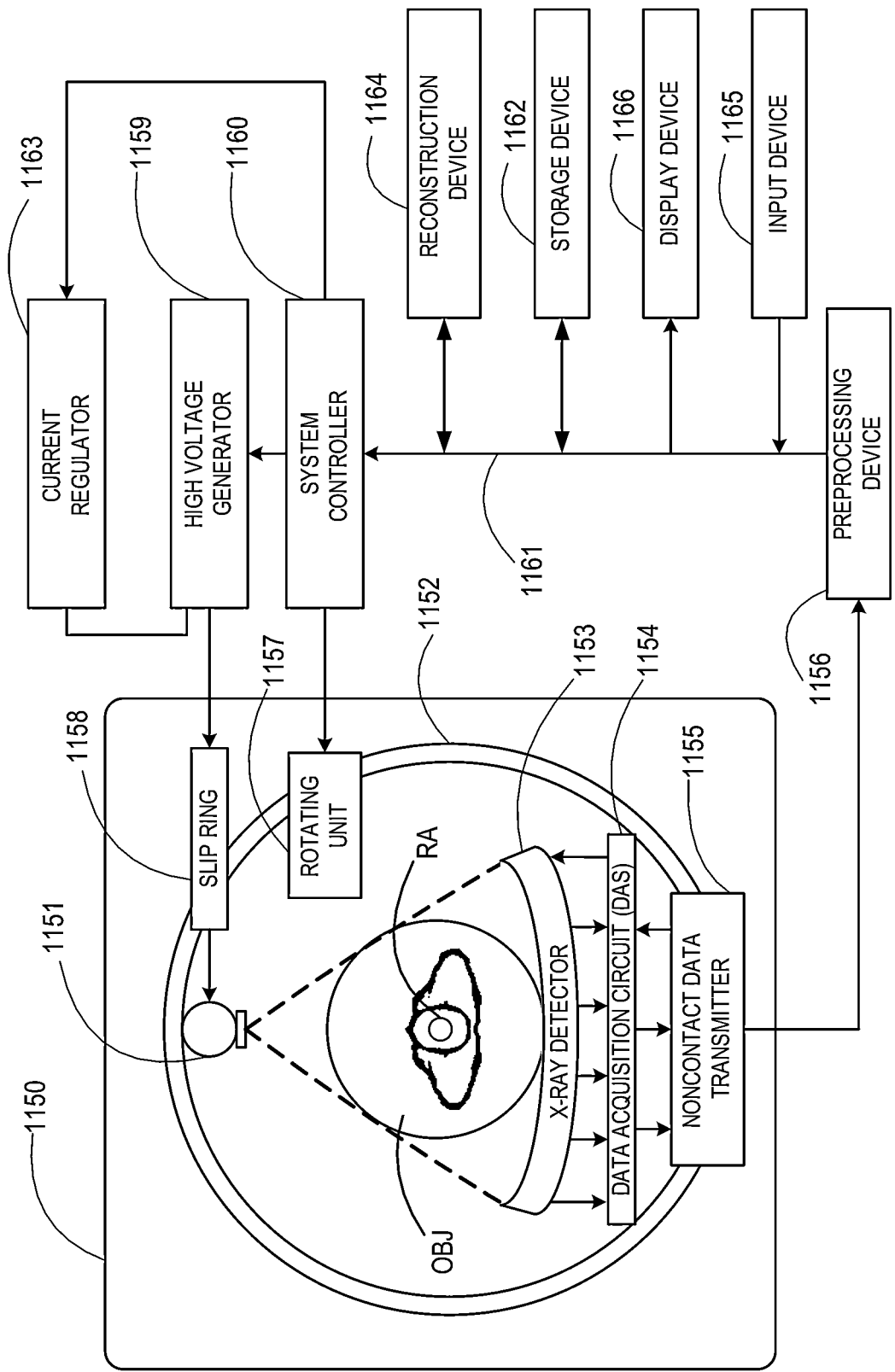
FIG. 11 shows a CT scanner system that can incorporate the techniques disclosed herein.

It can be appreciated that, in one embodiment, the above mentioned techniques can be applied to a CT apparatus or scanner. FIG. 11 illustrates an implementation of a horizontal radiography gantry included in a CT apparatus or scanner. As shown in FIG. 11, a radiography gantry 1150 (illustrated from a side view) includes an X-ray tube 1151, an annular frame 1152, and a multi-row or two-dimensional-array-type X-ray detector 1153. The X-ray tube 1151 and X-ray detector 1153 are diametrically mounted across an object OBJ (e.g., a patient) on the annular frame 1152, which is rotatably supported around a rotation axis RA. A rotating unit 1157 rotates the annular frame 1152 at a high speed, such as 0.4 sec/rotation, while the object OBJ (e.g., a patient) is being moved along the axis RA into or out of the illustrated page.

An embodiment of an X-ray CT apparatus according to the present inventions will be described below with reference to the views of the accompanying drawing. Note that X-ray CT apparatuses include various types of apparatuses, e.g., a rotate/rotate-type apparatus in which an X-ray tube and X-ray detector rotate together around an object to be examined, and a stationary/rotate-type apparatus in which many detection elements are arrayed in the form of a ring or plane, and only an X-ray tube rotates around an object to be examined. The present inventions can be applied to either type. In this case, the rotate/rotate-type, which is currently the mainstream, will be exemplified.

The multi-slice X-ray CT apparatus further includes a high voltage generator 1159 that generates a tube voltage applied to the X-ray tube 1151 through a slip ring 1158 so that the X-ray tube 1151 generates X-rays. An X-ray detector 1153 is located at an opposite side from the X-ray tube 1151 across the object OBJ (e.g., a patient) for detecting the emitted X-rays that have transmitted through the object OBJ (e.g., a patient). The X-ray detector 1153 further includes individual detector elements or units and may be a photon-counting detector. In the fourth-generation geometry system, the X-ray detector 1153 may be one of a plurality of detectors arranged around the object OBJ (e.g., a patient) in a 360° arrangement.

The CT apparatus further includes other devices for processing the detected signals from the X-ray detector 1153. A data acquisition circuit or a Data Acquisition System (DAS) 1154 converts a signal output from the X-ray detector 1153 for each channel into a voltage signal, amplifies the signal, and further converts the signal into a digital signal. The X-ray detector 1153 and the DAS 1154 are configured to handle a predetermined total number of projections per rotation (TPPR).

The above-described data is sent to a preprocessing device 1156, which is housed in a console outside the radiography gantry 1150 through a non-contact data transmitter 1155. The preprocessing device 1156 performs certain corrections, such as sensitivity correction, on the raw data. A memory 1162 stores the resultant data, which is also called projection data at a stage immediately before reconstruction processing. The memory 1162 is connected to a system controller 1160 through a data/control bus 1161, together with a reconstruction device 1164, input device 1165, and display 1166. The system controller 1160 controls a current regulator 1163 that limits the current to a level sufficient for driving the CT system. In an embodiment, the system controller 1160 implements optimized scan acquisition parameters, as described above. The reconstruction device 1164 can include circuitry configured to perform the above mentioned techniques, such as method 600.

The method and system described herein can be implemented in a number of technologies but generally relate to imaging devices and/or processing circuitry for performing the techniques described herein. In one embodiment, the processing circuitry is implemented as one of or as a combination of: an application specific integrated circuit (ASIC), a field programmable gate array (FPGA), a generic array of logic (GAL), a programmable array of logic (PAL), circuitry for allowing one-time programmability of logic gates (e.g., using fuses) or reprogrammable logic gates. Furthermore, the processing circuitry can include computer processor circuitry having embedded and/or external non-volatile computer readable memory (e.g., RAM, SRAM, FRAM, PROM, EPROM, and/or EEPROM) that stores computer instructions (binary executable instructions and/or interpreted computer instructions) for controlling the computer processor to perform the processes described herein. The computer processor circuitry may implement a single processor or multiprocessors, each supporting a single thread or multiple threads and each having a single core or multiple cores.

This disclosure presented a two-step material decomposition calibration method and apparatus design for a full size photon counting CT system with the following key components: slabs of known materials and thicknesses are used for the two-step material decomposition calibration in a 3rd generation PCD based CT system; slabs of each chosen material with a proper size to cover the entire detector surface are used for the calibration scans, where the slabs may need to be leveled during these scans; a static scan scheme with multiple X-ray tube park positions are designed to increase the calibration path lengths samples with each of the slab thickness; slabs with different thicknesses and materials can be stacked in the Z direction to speed up the calibration procedure; the calibration path length range is designed to cover the targeted scan object size/shape; the calibration path length samples or range can be the same for all the detector channels across the fan beam, or a sub-group of the samples can be used to target the path length range of the object scan for different detector channels; the samples that are used for the calibration and the resulted tables can be imaging task specific; to correct the shadow differences between the static calibration scans and the rotating object scans, air scans at the same data acquisition condition are performance to extract the detection geometric efficiency factors at each rotation speed, while a reference detector at the tube side can be used to provide the tube flux normalization like the way in the conventional CT systems.

Embodiments of the present disclosure may also be as set forth in the following parentheticals.

(1) A calibration method comprising: placing at least one slab in a field of view of an X-ray scanner system, wherein the at least one slab has at least one known linear attenuation coefficient and at least one known pathlength; scanning, on the X-ray scanner system, the at least one slab with at least one X-ray tube located at plural known locations at different angles relative to the at least one slab; generating material decomposition data based on the scannings at the different angles; generating air calibration data based on at least one air scan using the at least one X-ray tube at at least one rotation speed; and calibrating a forward model for the X-ray scanner system based on the material decomposition data and the air calibration data.

(2) The method of (1), wherein the at least one X-ray tube is stationary.

(3) The method of any (1) to (2), wherein the material decomposition data includes a weighted bin response and a pulse pileup correction term.

(4) The method of any (1) to (3), wherein the forward model includes a weighted bin response, a pulse pileup correction term, the at least one known linear attenuation coefficient, the at least one known pathlength, and the air calibration data.

(5) The method of any (1) to (4), wherein the at least one slab is placed level in the field of view of the X-ray scanner system.

(6) The method of any (1) to (5), wherein the at least one slab fully cover the field of view of the X-ray scanner system.

(7) The method of any (1) to (6), further comprising: scanning, after the calibrating of the forward model for the X-ray scanner system, an object.

(8) The method of any (1) to (7), wherein the at least one slab is made up of multiple materials.

(9) The method of any (1) to (8), wherein the X-ray scanner system is a photon counting CT scanner system.

(10) The method of any (1) to (9) wherein the at least one slab includes a plurality of slabs with different heights.

(11) A system comprising: at least one slab placed in a field of view of an X-ray scanner system, wherein the at least one slab has at least one known linear attenuation coefficient and at least one known pathlength; and processing circuitry configured to, scan, on the X-ray scanner system, the at least one slab with at least one X-ray tube located at plural known locations at different angles relative to the at least one slab; generate material decomposition data based on the scannings at the different angles; generate air calibration data based on at least one air scan using the at least one X-ray tube at at least one rotation speed; and calibrate a forward model for the X-ray scanner system based on the material decomposition data and the air calibration data.

(12) The system of (11), wherein the at least one X-ray tube is stationary.

(13) The system of any (11) to (12), wherein the material decomposition data includes a weighted bin response and a pulse pileup correction term.

(14) The system of any (11) to (13), wherein the forward model includes a weighted bin response, a pulse pileup correction term, the at least one known linear attenuation coefficient, the at least one known pathlength, and the air calibration data.

(15) The system of any (11) to (14), wherein the at least one slab is placed level in the field of view of the X-ray scanner system.

(16) The system of any (11) to (15), wherein the at least one slab fully covers the field of view of the X-ray scanner system.

(17) The system of any (11) to (16), wherein the processing circuitry is further configured to scan, after the calibrating of the forward model for the X-ray scanner system, an object.

(18) The system of any (11) to (17), wherein the at least one slab is made up of multiple materials.

(19) The system of any (11) to (18), wherein the X-ray scanner system is a photon counting CT scanner system.

(20) The system of any (11) to (19), wherein the at least one slab includes a plurality of slabs with different heights.

Numerous modifications and variations of the embodiments presented herein are possible in light of the above teachings. It is therefore to be understood that within the scope of the claims, the disclosure may be practiced otherwise than as specifically described herein.

The invention claimed is:

1. A calibration method, comprising:
placing a single slab of a single material in a field of view of an X-ray scanner system, wherein the slab has a known linear attenuation coefficient and a known pathlength;
scanning, with the X-ray scanner system, the slab with at least one X-ray tube located at plural known locations at different corresponding angles relative to the slab so as to scan the slab from the different corresponding angles;
repeating the placing and scanning steps for another single slab of the single material having a different thickness than the single slab,
generating material decomposition data based on the scannings at the different corresponding angles for the single slab and the another single slab;
generating air calibration data based on an air scan using the at least one X-ray tube at a rotation speed; and
calibrating a forward model for the X-ray scanner system based on the material decomposition data and the air calibration data.

2. The method of claim 1, wherein the at least one X-ray tube is stationary.

3. The method of claim 1, wherein the material decomposition data includes a weighted bin response and a pulse pileup correction term.

4. The method of claim 1, wherein the forward model includes a weighted bin response, a pulse pileup correction term, the known linear attenuation coefficient, the known pathlength, and the air calibration data.

5. The method of claim 1, wherein each slab is placed level the field of view of the X-ray scanner system.

6. The method of claim 1, wherein each slab fully covers the field of view of the X-ray scanner system.

7. The method of claim 1, further comprising:
scanning, after the calibrating of the forward model for the X-ray scanner system, an object.

8. The method of claim 1, wherein the X-ray scanner system is a photon counting CT scanner system.

9. An X-ray scanner system, comprising:
a single slab of a single material placed in a field of view of the X-ray scanner system, wherein the slab has a known linear attenuation coefficient and a known pathlength; and
processing circuitry configured to
scan, with the X-ray scanner system, the slab with at least one X-ray tube located at plural known locations at different corresponding angles relative to the slab so as to scan the slab from the different corresponding angles;
after another single slab of the single material having a different thickness than the single slab is placed in the field of view of the X-ray scanner system, repeat the scan with the X-ray scanner system;
generate material decomposition data based on the scannings at the different corresponding angles for the single slab and the another single slab;
generate air calibration data based on an air scan using the at least one X-ray tube at a rotation speed; and
calibrate a forward model for the X-ray scanner system based on the material decomposition data and the air calibration data.

10. The system of claim 9, wherein the at least one X-ray tube is stationary.

11. The system of claim 9, wherein the material decomposition data generated by the processing circuitry includes a weighted bin response and a pulse pileup correction term.

12. The system of claim 9, wherein the forward model includes a weighted bin response, a pulse pileup correction term, the known linear attenuation coefficient, the known pathlength, and the air calibration data.

13. The system of claim 9, wherein each slab is placed level in the field of view of the X-ray scanner system.

14. The system of claim 9, wherein each slab fully covers the field of view of the X-ray scanner system.

15. The system of claim 9, wherein the processing circuitry is further configured to cause the X-ray scanner system to scan, after the calibrating of the forward model for the X-ray scanner system, an object.

16. The system of claim 9, wherein the X-ray scanner system is a photon counting CT scanner system.

* * * * *